United States Patent
deVries

(10) Patent No.: US 7,597,660 B2
(45) Date of Patent: Oct. 6, 2009

(54) INCONTINENCE THERAPY

(75) Inventor: Jan Albert deVries, Zelhem (NL)

(73) Assignee: Broockeville Corporation B.V., Curacao (AN)

( * ) Notice: Subject to any disclaimer, the term of this patent is extended or adjusted under 35 U.S.C. 154(b) by 577 days.

(21) Appl. No.: 10/944,658

(22) Filed: Sep. 17, 2004

(65) Prior Publication Data
US 2005/0075533 A1    Apr. 7, 2005

Related U.S. Application Data

(60) Provisional application No. 60/504,349, filed on Sep. 19, 2003.

(51) Int. Cl.
*A61F 2/00* (2006.01)
*A61F 2/04* (2006.01)

(52) U.S. Cl. ............................ 600/29; 623/23.66

(58) Field of Classification Search ............. 623/23.66; 600/29
See application file for complete search history.

(56) References Cited

U.S. PATENT DOCUMENTS

| | | | |
|---|---|---|---|
| 4,245,623 A | 1/1981 | Erb | |
| 5,571,182 A * | 11/1996 | Ersek et al. | 623/23.73 |
| 5,705,488 A | 1/1998 | Janzen et al. | |
| 6,030,416 A | 2/2000 | Huo et al. | |
| 6,071,230 A * | 6/2000 | Henalla | 600/29 |
| 6,361,561 B1 * | 3/2002 | Huo et al. | 623/6.56 |
| 6,533,819 B1 | 3/2003 | Urry et al. | |
| 6,613,343 B2 * | 9/2003 | Dillingham et al. | 424/427 |

FOREIGN PATENT DOCUMENTS

| | | |
|---|---|---|
| DE | 199 25 162 A1 | 6/1999 |
| GB | 1 297 350 | 5/1971 |
| WO | WO 01/76651 A1 | 10/2001 |

* cited by examiner

*Primary Examiner*—Thomas J Sweet
(74) *Attorney, Agent, or Firm*—Troutman Sanders LLP; Ryan A. Schneider; James Hunt Yancey, Jr.

(57) ABSTRACT

Urinary incontinence such as stress incontinence, is alleviated in a mammal, in particular a human being, especially a woman, by correcting the internal urethral orifice and the urethra with an elastic form stable material. Such a material preferably a curable elastomer-precursor composition is injected in the body tissue surrounding the urethra, thereby correcting internal urethral orifice and the urethra substantially to its original shape, allowing the sphincter to act in a controllable way.

6 Claims, 3 Drawing Sheets

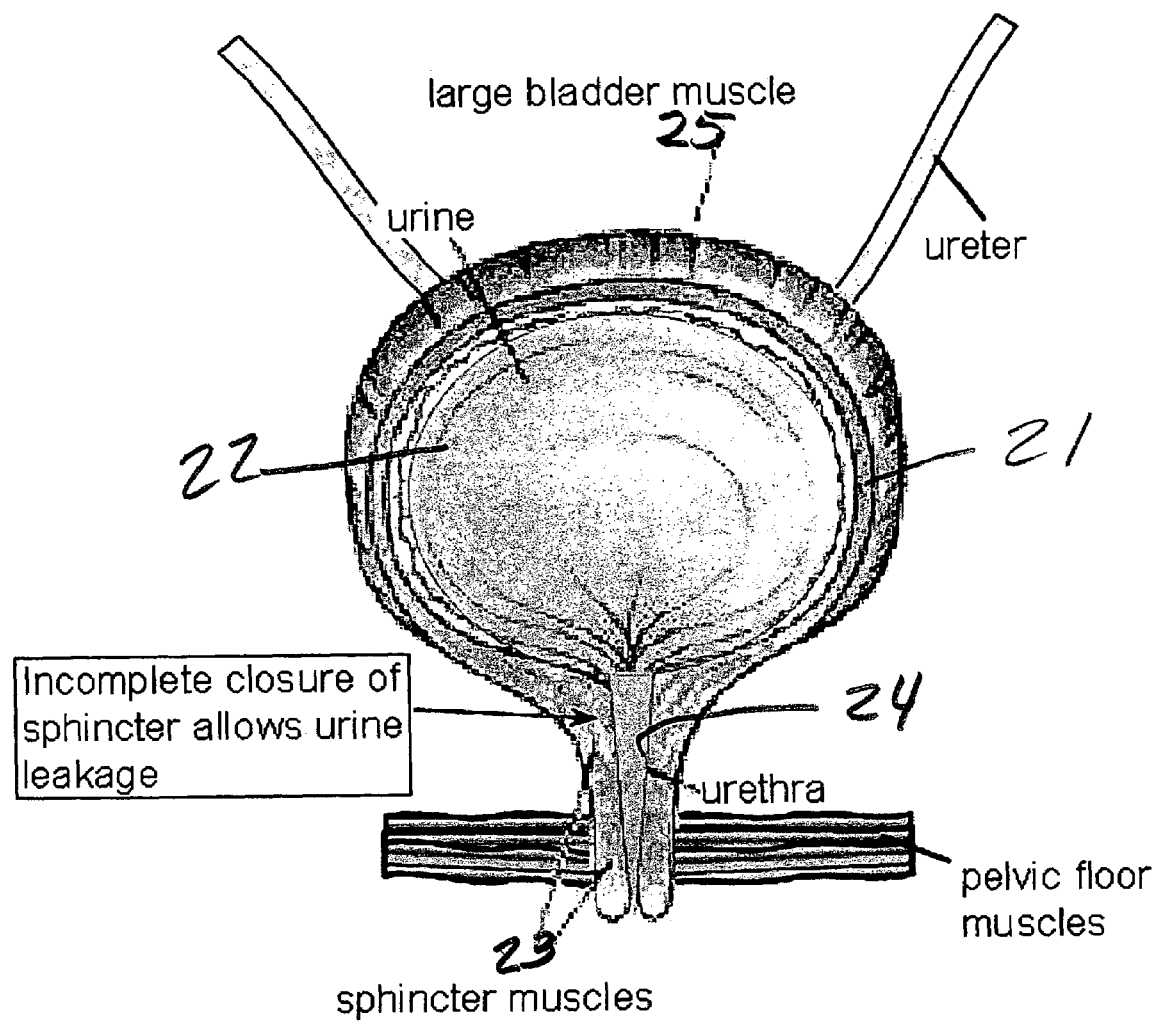

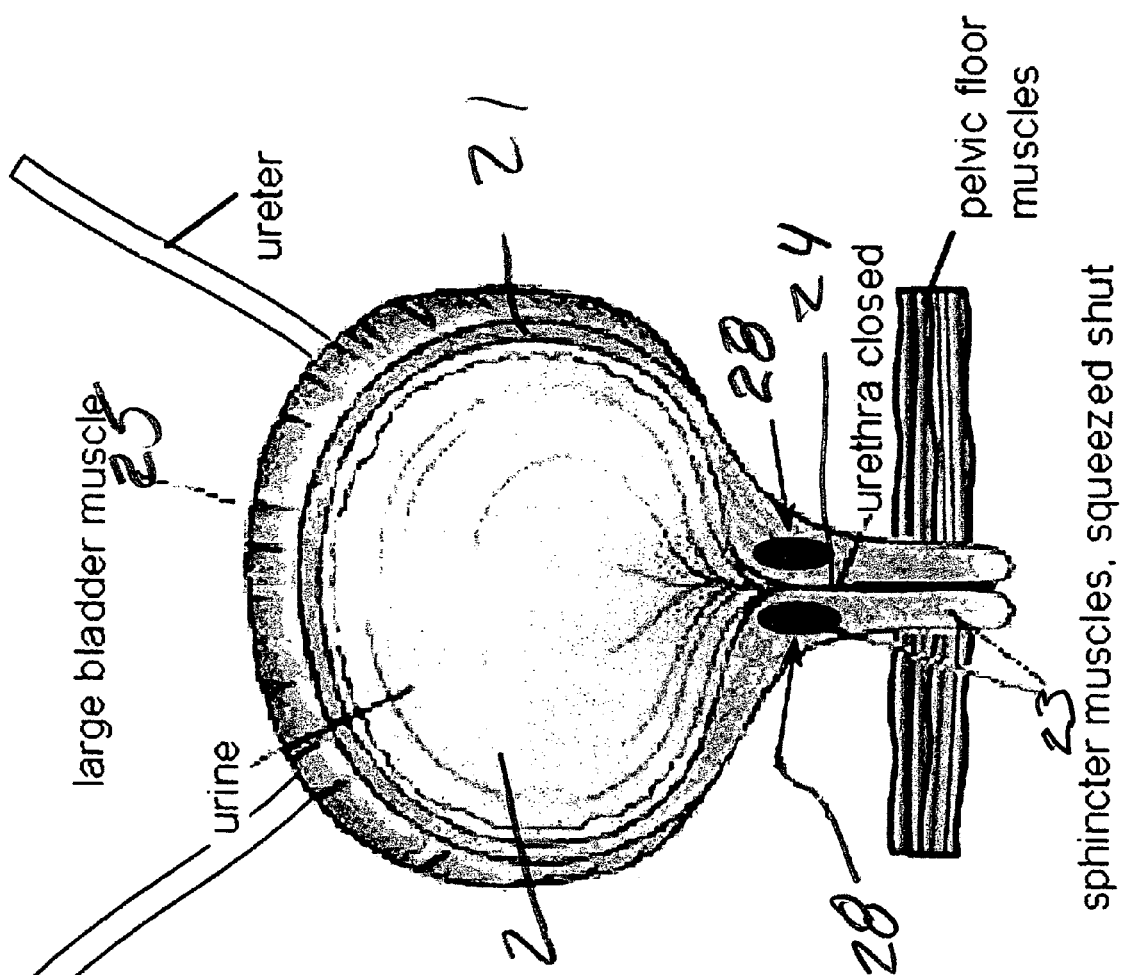

INCONTINENCE THERAPY

RELATED APPLICATIONS

This application is related to U.S. Provisional Patent Application Ser. No. 60/504,349, filed Sept. 19, 2003 entitled INCONTINENCE THERAPY.

TECHNICAL FIELD

The present invention relates to a method of treating urinary incontinence, in particular stress incontinence, in mammals, in particular human beings, especially females. This invention also relates to a composition suitable for use in such a method, its preparation and use.

BACKGROUND ART

Stress incontinence is a phenomenon which frequently occurs in human beings, in particular elder human beings. This uncontrolled and unvoluntary leakage of urine is related to physical activities which strain the abdominal muscles such as coughing, sneezing, lifting of heavy objects, climbing of stairs, etc. The sphincter cannot sufficiently contract in order to resist the increased tension in the abdomen including enlarged tension on the bladder, and undesirable loss of urine is the result. This condition is more common in the female population and is usually associated with weakened pelvic floor muscles related to multiple births and menopause. Also a deficiency of certain female hormones (estrogens) during the menopause can effect the sphincter of the bladder. In the male population, it may be related to certain surgical procedures. Obesity, e.g. derived from diabetus mellitus is another possible cause. Although stress incontinence is usually a periodically occuring phenomenon, the leaking can worsen and become constant.

In order to treat this kind of incontinence various therapies exist. Examples thereof comprise physiotherapy in order to strengthen the pelvic floor muscles by exercise and training. Therapy with hormones is another example. Lowering of the uterus can be counteracted by a pessarium. However, if these therapies do not have the desired effect, surgery is a further option. One of the surgical options is the application of a tension free vaginal tape. This tape is positioned at a position under the urethra, and supports this during activities such as coughing, laughing and lifting.

Another surgical method comprises so-called colposuspensions, e.g. according to Burch, wherein the mouth of the urethra is raised and suspended to the inner side of the pubic bone. Other physicians are also using injections of collagen or silicone particles in the wall of the urethra to bulk up the urethra and try to limit leakage that way. Thereby the cross dimension of the urethra is reduced, as a result of which the urine can flow less easily from the bladder. However, collagen is resorbable by the body, as a result of which it is apt to reduce its action. Particles, such as the silicone particles are apt to migrate in the body. Thus their position is not maintained, as a result of which the effect is not ensured, and even reduced in time.

Although some of the treatments mentioned above have shown to be successful at least initially at the start of the treatment, the success rate is not easy to predict. Moreover, as the general bodily condition of a patient suffering from incontinence may change over the years, the effectiveness of a certain therapy may become less. In particular injection of particulate material has not been attractive to patients and therefore has not been accepted broadly. Moreover, it is known that the success rate of this kind of treatment is far less compared to the other techniques mentioned above.

As a consequence, there is still a continued need for alternative methods in addition to the existing methods of counteracting stress incontinence, in particular methods which are easy to perform.

There is also a continued need for materials which are effective in counteracting stress incontinence when applied to a mammal, such as a human being.

SUMMARY OF THE INVENTION

In accordance with the present invention, there is provided a method of treating incontinence in a mammal including human beings, in particular women, comprising a step of correcting the shape of the internal urethral orifice and the urethra with an elastic form stable material, preferably comprising a curable elastomer-precursor composition. According to the invention, human beings in particular elder women suffering from stress incontinence, are treated by remodeling of the internal urethral orifice (the transition from the bladder to the urethra) and urethra into a shape wherein the effect of the force applied by the sphincter to the urethra and bladder in order to keep it closed, is enhanced. This favourabe shape of the urethra is permanently induced by the form stable material. After curing this non-resorbable material is a solid mass compared to particulate material and cannot migrate through the body, but holds its initial position where it is applied. Simultaneously the form stable material itself is flexible enough to adapt to body movements, so that a patient treated according to the invention does not experience any discomfort.

This elastic form stable material preferably comprises an elastomer-precursor composition which is cured in situ. That is to say, the elastomer precursor is prepared in advance and then applied to the appropriate positions by suitable equipment. At these positions the curing of the material thus applied is completed. Surprisingly, it was found that a form stable material made from an elastomeric composition not only is more convenient to the patient treated, but also allows to remodel the internal urethral orifice and the urethra into its original shape wherein forces exerted by the sphincter are sufficient to prevent leakage of urine.

The invention also relates to a method of preparing a composition for the treatment of incontinence in a mammal, in particular human beings, especially women, which composition comprises an elastic form stable material, preferably a curable elastomer-precursor-composition. Said treatment of incontinence is the shape correction of the urethra and internal urethral orifice.

A further aspect of the invention concerns the use of elastic form stable material, preferably a curable elastomer-precursor composition, in the treatment of urinary incontinence in mammals, in particular human beings, especially women.

THE DRAWINGS

For a fuller understanding of the nature and objects of the invention, reference should be had to the following detailed description taken in connection with the accompanying drawings, in which:

FIG. 2 is a diagramatic view showing a bladder and urethra, with the bladder filled with urine, in an individual suffering from incontinence; and FIG. 3 is a diagramatic view showing the bladder and urethra of FIG. 2, after treatment in accordance with the present invention.

DESCRIPTION OF THE PREFERRED EMBODIMENTS

Figure 1:
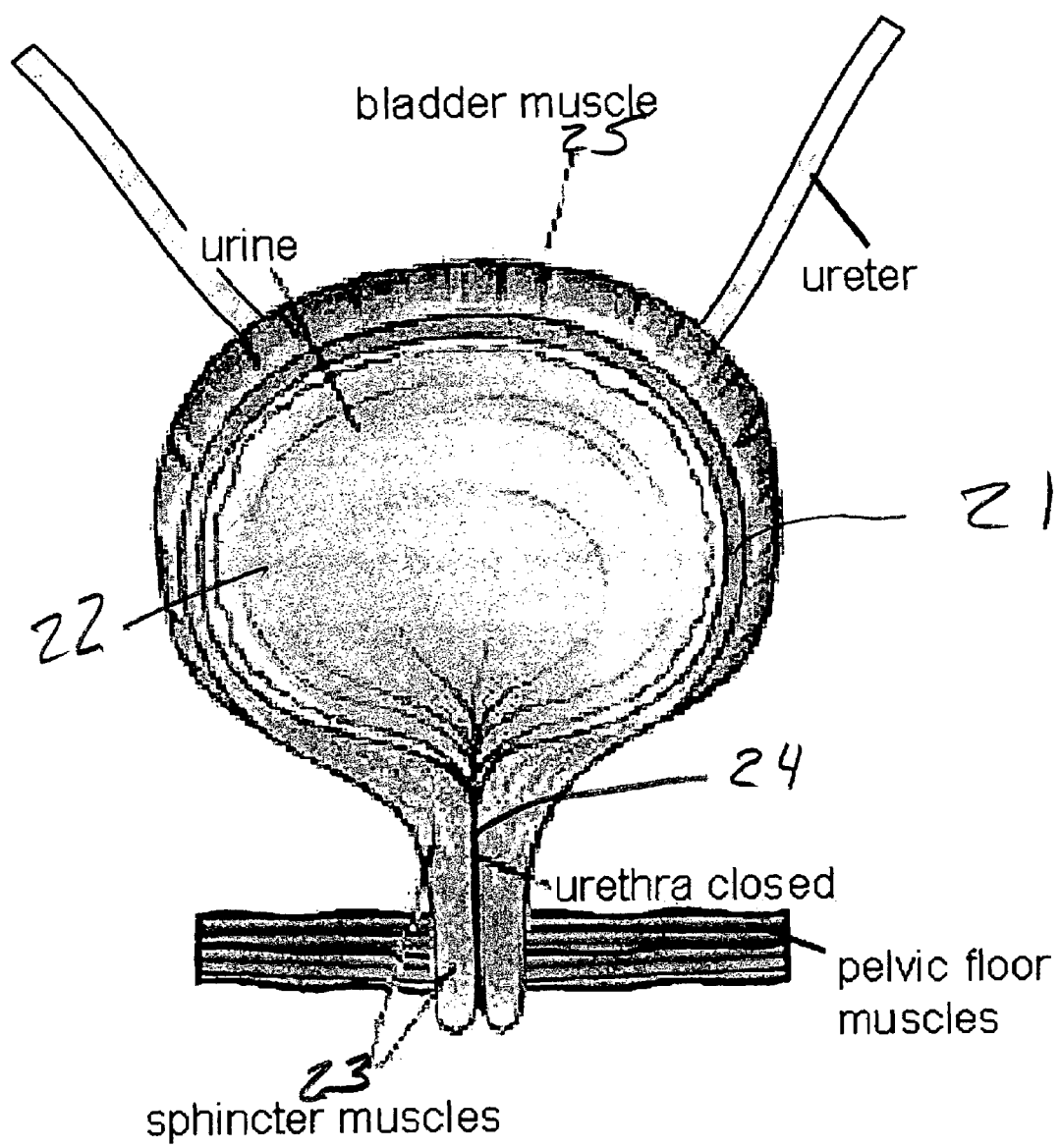
FIG. 1 is a diagramatic view showing a normal bladder and urethra, with the bladder filled with urine.

According to a preferred embodiment, the correction step comprises injecting a curable elastomer-precursor composition in the body tissue surrounding the urethra. Contrary to the collagen and silicone therapies according to the state of the art, wherein the composition is applied in the wall of the urethra, the correcting composition according to the invention is injected through the wall of the urethra in the tissue directly adjacent to the urethra. Preferably the composition is injected in at least three periheral positions in order to allow said correction. More preferably several injections are carried out in such a way that the cured composition completely surrounds the urethra as an annular support.

Commercially available medical grade silicone elastomers are preferred materials for use as polymer precursor in the remodeling composition. A more preferred material is poly (dimethyl siloxane) such as hydroxyl-end-blocked poly(dimethyl siloxane). Such silicone elastomers of medical grade as pourable, two-component silicone are available from e.g. NuSil Technology. These silicone elastomers are fast curing materials. For these types of elastomers propyl orthosilicate is a useful cross-linking agent. Fillers and diluents (medicinal fluids such as known under the trade name Dimeticonum) in order to reduce viscosity may be added as needed. An initiator like tin (II) octoate initiates the polymerisation reaction with splitting of propanol. The reaction proceeds without the generation of sensible heat. Silphenylene polymer can be used in a similar way. In order to be able to trace by X-ray monitoring the position of the cured applied composition, in a preferred embodiment the composition comprises a radiopaque material, such as silver powder, barium sulfate or bismuth trioxide.

Here it is noted that a composition as explained above is known per se as a material suitable for the non-surgical, reversible sterilization of females. In this known sterilization method the composition is injected in the oviduct portion adjacent the uterus, where it forms in situ a block or plug in the oviduct, thereby preventing the passage of ovum from the ovaries to the uterus and sperm from entering the oviduct and thus conception. See e.g. U.S. Pat. No. 4,245,623.

A preferred composition for use in the method according to the invention comprises about 60-75% by weight poly(dimethyl siloxane), about 2-5% cross-linking agent, a diluent in the range of 10-20% and about 10-20% radiopaque powder. An even more preferred composition comprises about 68 wt. % poly(dimethyl siloxane), about 4% cross-linking agent, about 13% dimeticonum and about 16% silver powder In the method according to the invention the composition is advantageously prepared in advance in a mixing-dispensing device. Such a device, wherein the function of mixing the components is combined with the function of dispensing the thus prepared mixture is known per se, e.g. from the above US patent, the content of which is incorporated in its entirety by reference.

As already indicated above, the invention also relates to a method of preparing a composition for the treatment of incontinence, in particular stress incontinence, in mammals in particular human beings, especially women, which composition comprises an elastic form stable composition, preferably a curable elastomer-precursor composition. The above-mentioned preferred features of the treatment method according to the invention are similarly applicable to the preparation method according to the invention.

Advantageously the correcting composition is packaged as a kit of parts, comprising at least a first container filled with an elastomer precursor and optionally a diluent, and a second container filled with a cross-linking agent for this elastomer precursor. More preferably, the composition is packaged in a mixing-dispensing device, comprising such containers and a temporarily seal between the containers, wherein one of these containers is provided with a stirrer which can be operated manually or powered by an external source. An example of such a device is also known from the above-mentioned US patent.

Devices of this type can be used for injecting the thus prepared precursor composition by connecting a suitable flexible tube to the container acting as a mixing chamber and providing an appropriate needle at the other end of the tube.

In the invention a flowable composition is prepared from the various components, preferably in a combined mixing-dispensing device as explained above, and then immediately used. The patient is prepared for the treatment according to standard medical procedures. A catheter is brought into the urethra until the injection needle reaches the bladder, e.g. indicated by the presence of a droplet of urine, and then retracted over a predetermined distance, e.g. in the range of 1-2 cm. At the position thus reached the wall of the urethra is punctured by the injection needle, and the composition is forced from the respective container via a suitable flexible tube to the needle and deposited directly adjacent this wall in the respective tissue. In order to more accurately position the deposit of the composition, preferably the needle is not open at the tip but has one or more exits at the side face directly adjacent to the tip. Use of this modified needle allows to position the composition more easily adjacent the urethra wall. Thereafter the needle is retracted and the composition is allowed to cure in situ. As already mentioned preferably the composition is applied at multiple locations surrounding the urethra. In view thereof the above actions can be repeated as needed.

By referring to FIGS. 1-3, along with the following detailed discussion, both the use and efficacy of the present invention can best be understood. As shown in FIG. 1, an individual, who does not suffer from incontinence, is able to completely retain urine 22 in bladder 21 by use of sphincter muscles 23. In such individuals, urine 22 is forced out of bladder 21 through urethra 24 by controlling sphincter muscles 23 and bladder muscles 25.

As discussed above, many individuals suffer from incontinence due to the inability of their sphincter muscles 23 to operate in the normal manner. As a result, as depicted in FIG. 2, urine 22 is able to leak through urethra 24 due to the inability of sphincter muscles 23 to maintain urethra 24 completely closed, as desired.

In order to eliminate this leakage problem, which plagues numerous individuals, the treatment provided by the present invention has been developed. As detailed above, by injecting a curable elastomer-precursor composition 28 into the tissue surrounding the urethra, in the area adjacent the bladder, normal control of the sphincter muscles is reestablished.

As shown in FIG. 3, and fully detailed above, the desired curable elastomer-precursor composition 28 is injected into the tissue surrounding urethra 24 in a plurality of separate and independent locations. In the preferred method, at least three locations are employed, with the injection site locations defining a substantially annular shape about urethra 24. By employing this method, it has been found that substantially normal control over sphincter muscles 23 are reestablished, and the incontinence problems that had previously existed are substantially eliminated.

Although the curable elastomer-precursor composition employed can be widely varied and the precise number and location of injection sites about urethra 24 may also be widely varied, all such alterations and/or variations are encompassed within the scope of the present invention. Although the preferred composition and injection site locations are detailed herein, the present invention is intended to encompass all variations coming within the overall disclosure of this invention.

It will thus be seen that the objects set forth above, among those made apparent from the preceding description, are efficiently attained and, since certain changes may be made in carrying out the above method without departing from the scope of the invention, it is intended that all matter contained in the above description, or shown in the accompanying drawings, shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

Having described my invention, what I claim as new and desire to secure by Letters Patent is:

1. A method of counteracting incontinence in a mammal, the method comprising:

correcting the shape of the internal urethral orifice and urethra with an elastic form stable material;

injecting a curable elastomer-precursor composition in the body tissue surrounding the urethra, wherein said curable elastomer-precursor composition comprises a silicone elastomer, a cross-linking agent, and a diluent, and wherein said curable elastomer-precursor composition is further defined as comprising between about 60% and 75% by weight based on the weight of the entire composition of poly(dimethyl siloxane), between about 2% and 5% by weight based upon the weight of the entire composition of a cross-linking agent, between about 10% and 20% by weight based upon the weight of the entire composition of a diluent, and between about 10% and 20% by weight based upon the weight of the entire composition of a radiopaque powder; and allowing said composition to cure in situ into a solid mass.

2. The method defined in claim 1, wherein said curable elastomer-precursor composition is injected at least in three positions.

3. The method defined in claim 2, wherein said curable elastomer-precursor composition is further defined as being injected at three positions which positions peripherally surround the urethra.

4. The method defined in claim 1, wherein said curable elastomer-precursor composition is further defined as being injected about the urethra in a substantially annular array.

5. The method defined in claim 1, wherein said curable elastomer-precursor composition is further defined as comprising at least two components which are intermixed in advance in a combined mixing dispensing device and then dispensed when needed.

6. The method according to claim 1, wherein the mammal is a woman.

* * * * *